United States Patent [19]

Allison et al.

[11] Patent Number: 4,772,466

[45] Date of Patent: * Sep. 20, 1988

[54] VACCINES COMPRISING POLYOXYPROPYLENE-POLYOXYETHYLENE BLOCK POLYMER BASED ADJUVANTS

[75] Inventors: Anthony C. Allison, Belmont; Noelene E. Byars, Sunnyvale, both of Calif.

[73] Assignee: Syntex (U.S.A.) Inc., Palo Alto, Calif.

[*] Notice: The portion of the term of this patent subsequent to Aug. 12, 2003 has been disclaimed.

[21] Appl. No.: 703,791

[22] Filed: Feb. 21, 1985

Related U.S. Application Data

[63] Continuation-in-part of Ser. No. 525,190, Aug. 22, 1983, Pat. No. 4,606,918.

[51] Int. Cl.$^4$ ............................................. A61K 39/39
[52] U.S. Cl. ................................... 424/88; 424/86; 424/87; 424/89; 424/90; 424/91; 424/92
[58] Field of Search ....................... 424/85-92; 514/8, 885; 436/543; 530/322, 806, 815

[56] References Cited

U.S. PATENT DOCUMENTS

| | | | |
|---|---|---|---|
| 3,867,521 | 2/1975 | Miskel et al. | 424/78 |
| 3,869,546 | 3/1975 | Lund | 424/88 |
| 3,869,549 | 3/1975 | Geller | 514/12 |
| 3,919,411 | 11/1975 | Glass et al. | 424/88 |
| 4,082,735 | 4/1978 | Jones et al. | 536/53 |
| 4,082,736 | 4/1978 | Jones et al. | 536/53 |
| 4,101,536 | 7/1978 | Yamamura et al. | 514/8 |
| 4,148,869 | 4/1979 | Deaton | 424/1.1 |
| 4,158,052 | 6/1979 | Audibert et al. | 424/88 |
| 4,185,089 | 1/1980 | Derrein et al. | 424/88 |
| 4,220,637 | 9/1980 | Audibert et al. | 424/88 |
| 4,314,998 | 2/1982 | Yamamura et al. | 424/88 |
| 4,323,559 | 4/1982 | Audibert et al. | 514/12 |
| 4,323,560 | 6/1982 | Baschang et al. | 424/88 |
| 4,369,178 | 1/1983 | Yamamura et al. | 514/8 |
| 4,382,080 | 5/1983 | Shiba et al. | 514/8 |
| 4,384,974 | 5/1983 | Guthauser et al. | 252/309 |
| 4,397,870 | 8/1983 | Sloviter | 514/672 |
| 4,406,889 | 9/1983 | Hartmann et al. | 424/88 |
| 4,409,209 | 10/1983 | Baschang et al. | 514/12 |
| 4,423,038 | 12/1983 | Baschang et al. | 514/8 |
| 4,427,659 | 1/1984 | Le Francier et al. | 514/8 |
| 4,461,761 | 7/1984 | Le Francier et al. | 514/8 |
| 4,578,269 | 3/1986 | Morein et al. | 424/88 |

FOREIGN PATENT DOCUMENTS

3308458-A 9/1984 Fed. Rep. of Germany.

OTHER PUBLICATIONS

Dukor et al., Annual Reports in Medicinal Chemistry-14, Chapter 15 (Immunostimulants), pp. 146-167.
Hunter, et al., *J. Immunol.*, 127, 1244, (1981).
Hunter, et al., *Rev. Cancer Res.*, 3, 279-286, (1980).
Snippe, et al., *Int. Archs. Allergy Appl. Immun.*, 65, 390-398, (1981).

*Primary Examiner*—John Kight
*Assistant Examiner*—Garnette D. Draper
*Attorney, Agent, or Firm*—Carol J. Roth; Tom M. Moran; Derek P. Freyberg

[57] ABSTRACT

A vaccine contains an immunologically effective amount of an antigen, a polyoxypropylene-polyoxyethylene block polymer, a glycol ether-based surfactant, an immunopotentiating amount of an immunostimulating glycopeptide, and, optionally, a metabolizable non-toxic oil.

28 Claims, No Drawings

VACCINES COMPRISING POLYOXYPROPYLENE-POLYOXYETHYLENE BLOCK POLYMER BASED ADJUVANTS

This application is a continuation-in-part of pending U.S. application Ser. No. 525,190 filed Aug. 22, 1983 now U.S. Pat. No. 4,606,918.

BACKGROUND OF THE INVENTION

This invention relates to vaccines. More particularly, this invention relates to a method for enhancing the immunogenicity of an antigen by emulsifying it with a polyoxypropylene-polyoxyethylene block polymer, a glycol ether-based surfactant, an optional metabolizable non-toxic oil, and an immunopotentiating amount of an immunostimulating glycopeptide.

RELATED DISCLOSURES

Freund's discovery that the immunogenicity of antigens could be potentiated by emulsifying an aqueous antigen solution with mineral oil alone or with mineral oil and *M. tuberculosis,* formed the basis of the concept of using a secondary material to increase a subject's humoral and cell-mediated immune responses to an antigen. An essential component of Freund's complete and incomplete adjuvant is mineral oil. This component plays a central role in effecting an increased humoral response to the antigen. However, mineral oil is believed to cause granulomas and other undesirable side effects. The mycobacteria in complete Freund's adjuvant are essential for significantly enhanced cellular immunity.

Though little attention was initially paid to the role the surfactant may play in Freund's incomplete or complete adjuvant, subsequent research has indicated that in several instances a surfactant may demonstrate adjuvant properties in and of itself. A number of naturally occurring surface active agents such as the lipid A portion of endotoxin of gram negative bacteria and trehalose dimycolate of mycobacteria are among the most potent adjuvants of these naturally occurring surfactants. A constituent of mammalian cells, the phospholipid lysolecithin also has been shown to have adjuvant activity. (B. Arnold et al, *Eur. J. Immunol.,* 9: 363–366 (1979).)

In addition, several synthetic surfactants, for example, dimethyldioctadecyl ammonium bromide (DDA) and certain polyoxypropylene-polyoxyethylene block polymers have been reported as having adjuvant activity. (See H. Snippe et al, *Int. Archs. Allergy Appl. Immun.,* 65: 390–398 (1981). In addition, R. Hunter et al, have reported in the *Journal of Immunology,* 127: 1244–1250 (1981) that polyoxypropylene-polyoxyethylene block polymers, when used as the surfactant component of an oil-in water based adjuvant formulation, increase antibody formation to Bovine serum albumin (BSA) in mice.

While these natural and synthetic surfactants demonstrate a certain degree of adjuvanticity, results so far published demonstrate that, except for DDA, none of the surfactants when used alone matches the immunopotentiating activity found when using complete or incomplete Freund's adjuvant. However, it is not possible to use either Freund's incomplete or complete adjuvant for general vaccination purposes because both mineral oil and mycobacteria have deleterious side effects when injected subcutaneously. As a result, Freund's adjuvants have not been authorized for domestic animal or human use by governmental regulatory agencies. Mineral oil is undesirable due to its side effects.

However, there is a substantial need for some means of potentiating the immunogenicity of antigens. This is particularly true because virus subunit and other protein antigens are now being prepared by recombinant DNA technology. Moreover, naturally occurring or synthetic peptide fragments from larger proteins known to be antigenic are being administered rather than whole proteins or a mixture of materials containing the whole proteins.

To elicit useful immune response, antigenic proteins and haptens must be administered with some type of adjuvant. Neither Freund's complete or incomplete adjuvant can be used, as noted above. Glycopeptides should be able to provide the needed immunopotentiation, but these materials are most effective when presented to the subject as an emulsion. Since mineral oil may not be used due to its toxicity, an alternative emulsion-forming material is needed for administering antigens.

It has now been found that when immunopotentiating glycopeptides and an antigen are emulsified with a non-toxic polyoxypropylene-polyoxyethylene block polymers and a multiphase-stabilizing amount of a glycol ether-based non-toxic surfactant, the immunogenicity of the antigen is increased in the same manner and to approximately the same degree as when mineral oil is used. It has been found that the block polymer is critical to achieving an immune response but that a maximal response is most effectively achieved only when the multiphase system is stabilized by some detergent such as a non-ionic glycol ether-based surfactant. The presence of a metabolizable oil may enhance the effectiveness of these formulations as well. Because the polyoxypropylene-polyoxyethylene block polymers and glycol ether surfactants are non-toxic, this adjuvant formulation may be safely used as a vehicle for enhancing the immunogenicity of antigens administered to birds and mammals.

SUMMARY OF THE INVENTION

One aspect of the invention is a vaccine for immunizing birds and mammals against viruses, bacteria, fungi, or parasites, which comprises an appropriate antigen emulsified with a polyoxypropylene-polyoxyethylene block polymer, a glycol ether-based surfactant, optionally a metabolizable non-toxic oil, and an immunopotentiating amount of an immunostimulating glycopeptide.

Another aspect of the invention is a method for enhancing the immunogenicity of an antigen which method comprises emulsifying the antigen with an adjuvant vehicle comprising an immunopotentiating amount of a glycopeptide, a multi-phase forming amount of a non-toxic polyoxypropylene-polyoxyethylene block copolymer, a multiphase-stabilizing amount of a glycol ether-based surfactant, optionally a metabolizable oil, and buffered aqueous solution in a quantity sufficient to make volume.

Another aspect of the invention is the method of immunizing a bird or mammal, by administering to said bird or mammal an immunogenic amount of a vaccine of the invention.

DETAILED DESCRIPTION

As set out above, the uniqueness of this invention lies in the use of a polyoxypropylene-polyoxyethylene block polymer in combination with a second surfactant such as a glycol ether-based surfactant as an adjuvant vehicle which, when formed into an emulsion or suspension with an immunopotentiating glycopeptide and an antigen, potentiates the immunogenicity of the antigen. This composition is further unique in that it can be safely administered to birds and mammals. Thus it is possible to prepare injectable vaccines wherein the antigen will elicit humoral and cell mediated immune responses comparable to those that can be obtained if the antigen is administered in Freund's incomplete or complete adjuvant. A vaccine with such properties will serve to reduce the number of times an antigen must be administered in order to develop a protective response in the subject. In addition, the amount of antigen required to elicit a protective response can be reduced.

The polyoxypropylene-polyoxyethylene (POP-POE) block polymers of this invention are a widely available material commercially known by the trademark Pluronic® polyols. These compounds are made by the sequential addition of propylene oxide and then ethylene oxide to a low molecular weight, reactive dihydroxy compound, usually propylene glycol. The characteristics of these polyols are determined by the molecular weight of the polyoxyethylene midsection and of the ratio of polyoxypropylene to polyoxyethylene in the polymer. Polyoxypropylene polyols with a molecular weight of approximately 900 or more are water insoluble and impart hydrophobic characteristics to the polyol. The polyoxyethylene component, which usually constitutes from 10% to 90% of the total weight, imparts water-soluble properties to the polymer, thus resulting in a compound having surface active properties.

POP-POE block polymers may be represented empirically by the formula:

$$HO(CH_2CH_2O)_a(\underset{\displaystyle CH_3}{\underset{|}{C}}HCH_2O)_b(CH_2CH_2O)_cH$$

wherein a and c are statistically equal. These compounds can be prepared by the methods set out in U.S. Pat. No. 2,674,619 issued to Lunsted. The most common means of making the compound is to react a bifunctional initiator, e.g., propylene glycol, with propylene oxide in the presence of a catalytic amount of anhydrous sodium hydroxide and allowing the reaction to proceed until the desired molecular weight is obtained. A predetermined amount of ethylene oxide is then added to the same reaction pot to make the block polymer.

These block polymer polyols range in molecular weight from approximately 1,000 up to 16,000. The polymers of particular interest in this invention are those having an average molecular weight between about 2,000 and 15,500. Such materials are commercially available from several sources, for example, BASF-Wyandotte Corp., Parsippany NJ. and E. I. Du pont.

POP-POE polyols available from BASF-Wyandotte under the name PLURONTC® are identified by a letter prefix followed by a two or a three digit number. The letter prefixes are L, P and F and refer to the physical form of each polymer, L-liquid, P-paste, or F-flakeable solid. The two and three digit numbers are used to designate the average molecular weight of the polyoxypropylene hydrophobic midsection in comparison with the percent polyoxyethylene in the total molecular. For example, the first two digits or "L-101" indicate that the polyoxypropylene midsection has an average molecular weight of 3,250 while the third digit indicates that the polymer is 10% polyoxyethylene by weight (w/w). In "F-108," the "10" designates a polyoxypropylene midsection with an average molecular weight of 3,250 and the "8" designates that polyoxyethylene comprises 80% (w/w) of the total molecule.

The block polymers of greatest interest to this invention are those which are liquid over a temperature range between about 15°-40° C. In addition, polymer mixtures of liquid and paste, liquid, paste and flakeable solid or liquid and flakeable solid mixtures which are liquid within the specified temperature range have utility in this invention.

Preferred block polymers are those having a POP midsection ranging in molecular weight between about 2250 and 4300 and POE in an amount between about 1 and 30% (w/w). More preferred are those polymers wherein POP has a molecular weight falling between 3250 and 4000 and the POE component comprises 10-20%. The PLURONIC® polyols L-101, L-121 and L-122 fall within this definition. Most preferred are the polymers wherein POE comprises about 10% (w/w) of the polymer and the POP midsection has a molecular weight of about 4000 or about 3250, e.g., PLURONIC® polyols L-121 and L-101 respectively.

A multi-phase forming amount of polymer is that quantity which will form micelles, or more broadly, a system characterized as an emulsion or suspension. For the purposes of this invention, that amount is between 0.2% and 49% by volume. A more preferred amount is between 0.2% and 20% (v/v), though no more than 5% is even more preferred and 2.5% is most preferred.

The efficacy of these compositions can best be realized by employing a non-toxic, non-ionic detergent to stabilize the emulsion or suspension formed. If the block polymer alone is used, the antigen will show some increased immunogenicity but the effect will be smaller in comparison with the effect observed when the non-ionic detergent is present. This non-ionic detergent may also be characterized as an emulsifying or suspending agent in that it is present for achieving those two purposes and is present in a minor amount in comparison to the block polymer.

A substantial number of emulsifying and suspending agents are generally used in the pharmaceutical sciences. These include naturally derived materials such as gums from trees, vegetable protein, sugar-based polymers such as alginates and cellulose, and the like. Certain oxypolymers or polymers having a hydroxide or other hydrophilic substituent on the carbon backbone have surfactant activity, for example, povidone, polyvinyl alcohol, and glycol ether-based mono- and polyfunctional compounds. Long chain fatty acid-derived compounds form a third substantial group of emulsifying and suspending agents which could be used in this invention. Though any of the foregoing surfactants are useful so long as they are non-toxic, the glycol ether derived compounds are the preferred emulsifying agents in this invention.

The simplest member of the family of compounds based on the glycol ethers is ethylene oxide. The internal or cyclic ethers of the simplest glycol, ethylene glycol, mono- and diethers of ethylene glycol are also well-known. One important group of glycol ethers is the polyethylene glycols. The compounds of most interest herein are PEG 200, 300, 400, 600 and 900.

A particularly useful group of surfactants are the sorbitan-based non-ionic surfactants. These surfactants are prepared by dehydration of sorbitol to give 1,4-sorbitan which is then reacted with one or more equivalents of a fatty acid. The fatty acid substituted moiety may be further reacted with ethylene oxide to give a second group of surfactants.

The fatty acid substituted sorbitan surfactants are made by reacting 1,4-sorbitan with a fatty acid such as lauric acid, palmitic acid, stearic acid, oleic acid, or a similar long chain fatty acid to give the 1,4-sorbitan mono-ester, 1,4-sorbitan sesquiester or 1,4-sorbitan triester. The common name for these surfactants are for example sorbitan monolaurate, sorbitan monopalmitate, sorbitan monostearate, sorbitan monooleate, sorbitan sesquioleate, sorbitan trioleate. These surfactants are commercially available under the name SPAN ® or ARLACEL ®, usually with a letter or number designation which distinguishes between the various mono-, di- and triester substituted sorbitans.

SPAN and ARLACEL surfactants are hydrophilic and are generally soluble or dispersible in oil and tend to form water-in-oil emulsions. They are also soluble in most organic solvents. In water they are generally insoluble but dispersible. Generally these surfactants will have a hydrophilic-lipophilic balance (HLB) number between about 1.8 to 8.6. Such surfactants can be readily made by means known in the art or are commercially available from, for example, ICI America's Inc., Wilmington, Del. under the registered mark ATLAS ®.

A related group of surfactants comprises polyoxyethylene sorbitan monoesters and polyoxyethylene sorbitan triesters. These materials are prepared by addition of ethylene oxide to a 1,4-sorbitan monoester or triester. The addition of polyoxyethylene converts the lipophilic sorbitan mono- or triester surfactant to a hydrophilic surfactant generally soluble or dispersible in water and soluble to varying degrees in organic liquids.

These materials, commercially available under the mark TWEEN ®, are useful for preparing oil-in-water emulsions and dispersions, or for the solubilization of oils and making anhydrous ointments water-soluble or washable. The TWEEN ® surfactants may be combined with a related sorbitan monoester or triester surfactants to promote emulsion stability. TWEEN ® surfactants generally have a HLB value falling between 9.6 to 16.7. TWEEN ® surfactants are commercially available from a number of manufacturers, for example ICI America's Inc., Wilmington, Del. under the registered mark ATLAS ® surfactants.

A third group of non-ionic surfactants which could be used alone or in conjunction with SPAN ®, ARLACEL ® and TWEEN ® surfactants are the polyoxyethylene fatty acids made by the reaction of ethylene oxide with a long-chain fatty acid. The most commonly available surfactant of this type is solid under the name MYRJ ® and is a polyoxyethylene derivative of stearic acid. MYRJ ® surfactants are hydrophilic and soluble or dispersible in water like TWEEN ® surfactants. The MYRJ ® surfactants may be blended with TWEEN ® surfactants or with TWEEN ®/SPAN ® or ARLACEL ® surfactant mixtures for use in forming emulsions. MYRJ ® surfactants can be made by methods known in the art or are available commercially from ICI America's Inc.

A fourth group of polyoxyethylene based non-ionic surfactants are the polyoxyethylene fatty acid ethers derived from lauryl, acetyl, stearyl and oleyl alcohols. These materials are prepared as above by addition of ethylene oxide to a fatty alcohol. The commercial name for these surfactants is BRIJ ®. BRIJ ® surfactants may be hydrophilic or lipophilic depending on the size of the polyoxyethylene moiety in the surfactant. While the preparation of these compounds is available from the art, they are also readily available from such commercial sources as ICI America's Inc.

Other non-ionic surfactants which could potentially be used in the practice of this invention are for example: polyoxyethylene, polyol fatty acid esters, polyoxyethylene ether, polyoxypropylene fatty ethers, bee's wax derivatives containing polyoxyethylene, polyoxyethylene lanolin derivatives, polyoxyethylene fatty glycerides, glycerol fatty acid esters or other polyoxyethylene acid alcohol or ether derivatives of long-chain fatty acids of 12–21 carbon atoms.

As the adjuvant and the vaccine formulations of this invention are intended to be multi-phase systems, it is preferable to choose an emulsion-forming non-ionic surfactant which has an HLB value in the range of about 7 to 16. This value may be obtained through the use of a single non-ionic surfactant such as a TWEEN ® surfactant or may be achieved by the use of a blend of surfactants such as with a sorbitan mono-, di- or triester with a compatible polyoxyethylene sorbitan mono- or triester based surfactant; a sorbitan ester-polyoxyethylene fatty acid; a sorbitan ester in combination with a polyoxyethylene lanolin derived surfactant; a sorbitan ester surfactant in combination with a high HLB polyoxyethylene fatty ether surfactant; or a polyethylene fatty ether surfactant or polyoxyethylene sorbitan fatty acid.

It is more preferred to use a single non-ionic surfactant, most particularly a TWEEN ® surfactant, as the emulsion stabilizing non-ionic surfactant in the practice of this invention. The surfactant named TWEEN ® 80, otherwise known as polysorbate 80 for polyoxyethylene 20 sorbitan monooleate, is the most preferred of the foregoing surfactants.

Multiphase stabilization can usually be effected by having the surfactant present in an amount of 0.05% to 2.5% by weight (w/w). An amount of 0.2% to 1% is preferred.

The immune response stimulating glycopeptides of this invention are a group of compounds related to and derived from N-acetylmuramyl-L-alanyl-D-isoglutamine, which was determined by Ellouz et al, *Biochem. & Biophys. Res. Comm.*, Vol 59, 4, 1317 (1974) to be the smallest effective unit possessing immunological adjuvant activity in *M. tuberculosis*, the mycobacterial component of Freund's complete adjuvant. A number of dipeptide- and polypeptide-substituted muramic acid derivatives were subsequently developed and found to have immunostimulating activity.

Though these glycopeptides are a diverse group of compounds, they can be generally represented by the formula

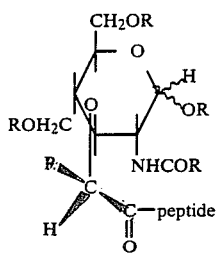

wherein the pyran ring oxygens are substituted by hydrogen, alkyl, or acyl or the like, or may be replaced by nitrogen-based substituents, particularly the 6-position oxygen; the 2-amino group is an acyl group or some other amide, the lactyl side chain is modified, e.g. is ethyl or another two-position alkyl moiety; and the peptide function is a dipeptide or polypeptide. Furanosyl analogs of the pyranosyl compounds also have immunopotentiating activity and are useful in this invention.

Among the glycopeptides of this invention are those disaccharides and tetrasaccharides linked by meso-α-ε-diaminopimelic acid such as described in U.S. Pat. Nos. 4,235,771 and 4,186,194.

Immune response stimulating glycopeptides which may be used in the practice of this invention are disclosed in U.S. Pat. Nos. 4,094,971; 4,101,536; 4,153,684; 4,235,771; 4,323,559; 4,327,085; 4,185,089; 4,082,736; 4,369,178, 4,314,998 and 4,082,735; and 4,186,194. The glycopeptides disclosed in these patents are incorporated herein by reference and made a part hereof as if set out in full herein. The compounds of Japanese patent application Nos. J5 4079-227, J5 4079-228, and J5 41206-696 would also be useful in the practice of this invention.

Methods for preparing these compounds are disclosed and well-known in the art. Preparative process exemplification can be found in U.S. Pat. Nos. 4,082,736 and 4,082,735. Additional, similar preparative processes may be found in the U.S. patents referenced in the preceding paragraph.

Preferred glycopeptides are those having the Formula I

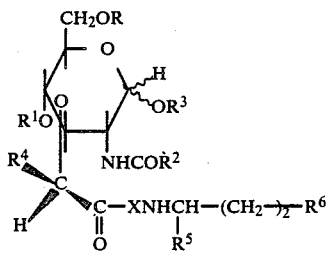

(I)

wherein

R and $R^1$ are the same or different and are hydrogen or an acyl radical containing from 1 to 22 carbon atoms;

$R^2$ is an unsubstituted or substituted alkyl radical containing from 1 to 22 carbon atoms, or an unsubstituted or substituted aryl radical containing from 6 to 10 carbon atoms;

$R^3$ is hydrogen, alkyl of 1 to 22 carbons, or aryl of 7 to 10 carbon atoms;

$R^4$ is hydrogen or alkyl;

X is alanyl, valyl, leucyl, isoleucyl, α-aminobutyryl, threonyl, methionyl, cysteinyl, glutamyl, glutaminyl, aspartyl, phenylalanyl, tyrosyl, tryptophanyl, lysyl, ornithinyl, arginyl, histidyl, asparaginyl, prolyl, hydroxyprolyl, seryl, or glycyl;

$R^5$ is an optionally esterified or amidated carboxyl group; and $R^6$ is an optionally esterified or amidated carboxyl group.

Alkyl is a straight or branched radical comprised of 1 to 7 carbon atoms unless otherwise specified, exemplified by methyl, ethyl, propyl, butyl, pentyl, hexyl or heptyl or an isomer. Lower alkyl is a radical of 1 to 4 carbon atoms.

An optionally esterified or amidated carboxyl group is the carboxyl group itself or a carboxyl group esterified with a lower alkanol, such as methanol, ethanol, propanol, butanol, or the carbamoyl group, which, on the nitrogen atom, is unsubstituted or mono-substituted or di-substituted by alkyl, especially lower alkyl, aryl, particularly phenyl, or arylalkyl, particularly benzyl. The carbamoyl group may also be substituted with an alkylidene radical such as butylidene or pentylidene radical. In addition, the carbamoyl group $R_5$ may also be substituted with a carbamoylmethyl group on the nitrogen atom.

Particularly preferred compounds are those of Formula 1 wherein R and $R^1$ are the same or different and are hydrogen or an acyl radical containing from 1 to 22 carbon atoms; $R^2$ is methyl; $R_3$ is hydrogen; and X is L-seryl, L-alanyl, L-valyl, L-leucyl, L-isoleucyl, L-α-aminobutyryl, L-seryl, L-threonyl, L-methionyl, L-cysteinyl, L-phenylalanyl, L-tyrosyl, L-tryptophenyl, L-lysyl, L-ornithyl, L-arginyl, L-histidyl, L-glutamyl, L-glutamanyl, L-aspartyl, L-asparaginyl, L-prolyl, or L-hydroxyprolyl.

A more preferred group of glycopeptides are the compounds of Formula 1 wherein R and $R^1$ are hydrogen or acyl of 1 to 22 carbon atoms, $R^2$ is methyl, $R^3$ is hydrogen, $R^4$ is methyl or butyl, and X is L-valyl, L-seryl, L-alanyl, L-threonyl or L-α-aminobutyryl.

Most particularly preferred are the following compounds:
N-acetylmuramyl-L-α-aminobutyryl-D-isoglutamine;
6-O-stearoyl-N-acetylmuramyl-L-α-aminobutyryl-D-isoglutamine;
N-acetylmuramyl-L-threonyl-D-isoglutamine;
N-acetylmuramyl-L-valyl-D-isoglutamine;
N-acetylmuramyl-L-alanyl-D-glutamine n-butyl ester;
N-acetyl-desmethyl-D-muramyl-L-alanyl-D-isoglutamine;
N-acetylmuramyl-L-alanyl-D-glutamine;
N-acetylmuramyl-L-seryl-D-isoglutamine;
N-acetyl(butylmuramyl)-L-α-aminobutyl-D-isoglutamine; and
N-acetyl(butylmuramyl)-L-alanyl-D-isoglutamine.

Hereinafter, N-acetylmuramyl-L-threonyl-D-isoglutamine shall be abbreviated [Thr¹]-MDP.

An effective amount of immunostimulating glycopeptide is that amount which effects an increase in titer level when administered in conjuntion with an antigen over that titer level observed when the glycopeptide has not been co-administered. As can be appreciated, each glycopeptide may have an effective dose range that may differ from the other glycopeptides. Therefore, a single dose range cannot be prescribed which will have a precise fit for each possible glycopeptide within the scope of this invention. However, as a general rule, the glycopeptide will preferably be present in the vaccine in an amount of between 0.001 and 5% (w/v). A more preferred amount is 0.01 to 3% (w/v).

Another component of these formulations, which may be present at the option of the formulator, is a metabolizable, non-toxic oil, preferably one of 6 to 30 carbon atoms including, but not limited to, alkanes, alkenes, alkynes, and their corresponding acids and alcohols, the ethers and esters thereof, and mixtures thereof. The oil may be any vegetable oil, fish oil, animal oil or synthetically prepared oil which can be metabolized by the body of the subject to which the adjuvant will be administered and which is not toxic to the subject. Mineral oil and similar toxic petroleum distillate oils are expressly excluded from this invention.

The optional oil component of this invention may be any long chain alkane, alkene or alkyne, or an acid or alcohol derivative thereof either as the free acid, its salt or an ester such as a mono-, di- or triester, such as the triglycerides and esters of 1,2-propanediol or similar poly-hydroxy alcohols. Alcohols may be acylated employing a mono- or poly-functional acid, for example acetic acid, propanoic acid, citric acid or the like. Ethers derived from long chain alcohols which are oils and meet the other criteria set forth herein may also be used.

The individual alkane, alkene or alkyne moiety and its acid or alcohol derivatives will have 6–30 carbon atoms. The moiety may have a straight or branched chain structure. It may be fully saturated or have one or more double or triple bonds. Where mono or poly ester- or ether-based oils are employed, the limitation of 6–30 carbons applies to the individual fatty acid or fatty alcohol moieties, not the total carbon count.

Any metabolizable oil, particularly from an animal, fish or vegetable source, may be used herein. It is essential that the oil be metabolized by the animal or bird to which it is administered, otherwise the oil component may cause abscesses, granulomas or even carcinomas, or may make the meat of vaccinated birds and animals unacceptable for human consumption due to the deleterious effect the unmetabolized oil may have on the consumer.

Sources for vegetable oils include nuts, seeds and grains. Peanut oil, soybean oil, coconut oil, and olive oil, the most commonly available, exemplify the nut oils. Seed oils include safflower oil, cottonseed oil, sunflower seed oil, sesame seed oil and the like. In the grain group, corn oil is the most readily available, but the oil of other cereal grains such as wheat, oats, rye, rice, triticale and the like may also be used.

The technology for obtaining vegetable oils is well developed and well known. The compositions of these and other similar oils may be found in, for example, the Merck Index, and source materials on foods, nutrition and food technology.

The 6–10 carbon fatty acid esters of glycerol and 1,2-propanediol, while not occurring nautrally in seed oils, may be prepared by hydrolysis, separation and esterification of the appropriate materials starting from the nut and seed oils. These products are commercially available under the name NEOBEE® from PVO International, Inc., Chemical Specialities Division, 416 Division Street, Boongon, N.J. and others. Reference is made to U.S. patent application Ser. No. 341,403, filed Jan. 21, 1982 for methods for making these latter materials.

Oils from any animal source, including birds, may be employed in the adjuvants and vaccines of this invention. Animal oils and fats are usually solids at physiological temperatures due to the fact that they exist as triglycerides and have a higher degree of saturation than oils from fish or vegetables. However, fatty acids are obtainable from animal fats by partial or complete triglyceride saponification which provides the free fatty acids. Fats and oils from mammalian milk are metabolizable and may therefore be used in the practice of this invention. The procedures for separation, purification, saponification and other means necessary for obtaining pure oils from animal sources are well known in the art.

Most fish contain metabolizable oils which may be readily recovered. For example, cod liver oil, shark liver oils, and whale oil such as spermaceti exemplify several of the fish oils which may be used herein. Shark liver oil contains a branched, unsaturated oil known as squalene, 2,6,10,15,19,23-hexamethyl-2,6,10,14,18,22-tetracosahexaene which is particularly preferred herein. Squalane, the saturated analog to squalene is also a particularly preferred oil. Fish oils, including squalene and squalane, are readily available from commercial sources or may be obtained by methods known in the art.

The oil component of these adjuvants and vaccine formulations will be present in an amount from 1% to 30% by weight but preferably in an amount of 1% w/w. It is most preferred to use a 5% w/w concentration of oil.

The aqueous portion of these adjuvant compositions is buffered saline. Because these compositions are intended for parenteral administration, it is preferable to make up these solutions so that the tonicity, i.e., osmolality, is essentially the same as normal physiological fluids in order to prevent post-administration swelling or rapid absorption of the composition because of differential ion concentrations between the composition and physiological fluids. It is also preferable to buffer the saline in order to maintain a pH compatible with normal physiological conditions. Also, in certain instances, it may be necessary to maintain the pH at a particular level in order to insure the stability of certain composition components such as the glycopeptides.

Any physiologically acceptable buffer may be used herein, but phosphate buffers are preferred. Other acceptable buffers such as acetate, tris, bicarbonate, carbonate, or the like may be used as substitutes for phosphate buffers.

The pH of the aqueous component will preferably be between 6.0–8.0 though it is preferable to adjust the pH of the system to 6.8 where that pH does not significantly reduce the stability of other composition components and is not otherwise physiologically unsuitable.

The quantity of buffered saline employed in these compositions will be that amount necessary to bring the value of the composition to unity. That is, a quantity of buffered saline sufficient to make 100% will be mixed with the other components listed above in order to bring the composition to volume.

The word antigen refers to any substance, including a protein or protein-polysaccharide, protein-lipopolysacchride, polysaccharide, lipopolysaccharide, viral subunit, whole virus or whole bacteria which, when foreign to the blood stream of a bird or animal, on gaining access to the tissue of such an animal stimulates the formation of specific antibodies and reacts specifically in vivo or in vitro with a homologous antibody. Moreover, it stimulates the proliferation of T-lymphocytes with receptors for the antigen, and can react with the lymphocytes to initiate the series of responses designated cell-mediated immunity.

A hapten is within the scope of this definition. A hapten is that portion of an antigenic molecule or antigenic complex that determines its immunological specificity. Commonly, a hapten is a peptide or polysaccharide in naturally occurring antigens. In artificial antigens it may be a low molecular weight substance such as an arsanilic acid derivative. A hapten will react specifically in vivo and in vitro with homologous antibodies or T-lymphocytes. Alternative descriptors are antigenic determinant, antigenic structural grouping and haptenic grouping.

The formulation of a vaccine of the invention will employ an effective amount of an antigen. That is, there will be included an amount of antigen which, in combination with the adjuvant, will cause the subject to produce a specific and sufficient immunological response so as to impart protection to the subject from the subsequent exposure to virus, bacterium, fungus, mycoplasm, or parasite immunized against.

Antigens may be produced by methods known in the art or may be purchased from commercial sources. For example, U.S. Pat. Nos. 4,434,157, 4,406,885, 4,264,587, 4,117,112, 4,034,081, 3,996,907, incorporated herein by reference, describe methods for preparing antigens for feline leukemia virus vaccines. Other antigens may similarly be prepared. Antigens within the scope of this invention include whole inactivated virus particles, isolated virus proteins and protein subunits, whole cells and bacteria, cell membrane and cell wall proteins, and the like. Vaccines of the invention may be used to immunize birds and mammals against diseases and infection, including without limitation cholera, diptheria, tetanus, pertussis, influenza, measles, meningitis, mumps, plague, poliomyelitis, rabies, Rocky Mountain spotted fever, rubella, smallpox, typhoid, typhus, feline leukemia virus, and yellow fever.

No single dose designation can be assigned which will provide specific guidance for each and every antigen which may be employed in this invention. The effective amount of antigen will be a function of its inherent activity and purity. It is contemplated that the adjuvant compositions of this invention may be used in conjunction with whole cell or virus vaccines as well as with purified antigens or protein subunit or peptide vaccines prepared by recombinant DNA technqiues or synthesis.

Adjuvant preparations are readily made by well known art methods. For example, one can make a 2-fold concentrated solution of the antigen and glycopeptide in the buffered saline. A two-fold concentration of the block polymer, oil, and multiphase stabilizing surfactant is mixed with buffered saline; then the first and second solution are mixed.

A further understanding of the invention may be had from the following non-limiting examples.

EXAMPLE 1

The activity of the adjuvant compositions was examined by means of a delayed hypersensitivy test and by an egg albumin (EA) antibody production test in guinea pigs. These two assays measure the ability of the adjuvant compositions to stimulate delayed hypersensitivity (DH, cell mediated response) and antibody synthesis (Ab, humoral immune response) in response to specific antigens in guinea pigs. The two tests were as follows: groups of 8 female guinea pigs were injected subcutaneously with EA emulsified in the adjuvant composition. Appropriate controls were included. The animals were subsequently skin tested with EA to measure delayed hypersensitivity, and were bled to obtain serum for antibody titrations.

Standard bioassay procedures were set up as follows: EA (200 micrograms per animal) was dissolved in saline and then emulsified with each of the six following adjuvant compositions.

TABLE 1

| First Test Composition | |
|---|---|
| Components | Quantity |
| [Thr$^1$]-MDP | 250 µg |
| TWEEN ® 80 | 2 µl |
| PLURONIC ® L-121 | 25 µl |
| Squalene | 50 µl |
| Phosphate buffered saline qs | 1000 µl |

TABLE 2

| Second Test Composition | |
|---|---|
| Components | Quantity |
| [Thr$^1$]-MDP | 250 µg |
| TWEEN ® 80 | 2 µl |
| PLURONIC ® L 121 | 25 µl |
| Phosphate buffered saline qs | 1,000 µl |

TABLE 3

| Third Test Composition | |
|---|---|
| Components | Quantity |
| [Thr$^1$]-MDP | 250 µg |
| TWEEN ® 80 | 2 µl |
| Squalene | 50 µl |
| Phosphate buffered saline qs | 1,000 µl |

TABLE 4

| Fourth Test Composition | |
|---|---|
| Components | Quantity |
| [Thr$^1$]-MDP | 250 µg |
| PLURONIC ® L-121 | 25 µl |
| Squalene | 50 µl |
| Phosphate buffered saline qs | 1,000 µl |

TABLE 5

| Fifth Test Composition | |
|---|---|
| Components | Quantity |
| PLURONIC ® L-121 | 250 µl |
| Squalene | 50 µl |
| Phosphate buffered saline qs | 1,000 µl |

TABLE 6

| Sixth Test Composition | |
|---|---|
| Components | Quantity |
| [Thr$^1$]-MDP | 250 µg |
| PLURONIC ® L 121 | 25 µl |
| Phosphate buffered saline qs | 1,000 µl |

0.2 ml of emulsion were administered per guinea pig. A booster injection of egg albumin in saline was given at 4 weeks. Blood samples were drawn at three and six weeks to determine EA antibody titers. The egg albumin skin test was carried out at six weeks.

EXAMPLE 2

The effect of squalene on antibody activity was determined in the experiment set forth below. The procedure described in Example 1 was used in this study.

TABLE 8

| Components | Quantity |
| --- | --- |
| [Thr$^1$]-MDP | 250 μg |
| TWEEN ® 80 | 2 μl |
| PLURONIC ® L-121 | 25 μl |
| Squalene | 50 μl |
| PBS qs | 1000 μl |

TABLE 9

| Components | Quantity |
| --- | --- |
| [Thr$^1$]-MDP | 250 μg |
| TWEEN ® 80 | 2 μl |
| PLURONIC ® L-121 | 25 μl |
| PBS qs | 1000 μl |

TABLE 10

| Components | Quantity |
| --- | --- |
| TWEEN ® 80 | 2 μl |
| PLURONIC ® L-121 | 25 μl |
| PBS qs | 1000 μl |

Egg albumin was mixed with the above formulations and 0.2 ml injected (S.C.) per guinea pig. A booster injection of egg albumin was given at 4 weeks. Animals were bled at 4 and 6 weeks to determine antibody titres, and skin tested with egg albumin at 6 weeks to measure delayed hypersensitivity.

EXAMPLE 3

Groups of 6 or 7 female guinea pigs, 400–500 g, were immunized with 200 μg of egg albumin (EA) in one of 4 vehicles. The basic vehicle mixture consisted of 0.2 ml of phosphate buffered saline with 0.2% TWEEN ®80 containing 10 μl of squalene (SQE) or squalane (SQA) and 5 μl of Pluronic ®L-121. Two test groups were also given 50 μg/animal of the glycodipeptide N-acetyl-muramyl-L-α-aminobutyryl-D-isoglutamine. The animals were boosted with 50 μg EA in saline on Day 28. On days 21, 35, and 50 the animals were bled by heart puncture and the sera assayed using the passive hemagglutination technique. On days 35 and 50 the animals were also skin tested with 10 μg EA injected ID. The skin tests were measured at 24 hours.

From the observations in these three Examples, it is clear that to elicit a powerful cell-mediated and humoral response, the combination of glycopeptide and PLURONIC ® polyol is essential. Further, cell-mediated and humoral response can be maximized by employing a metabolizable oil.

EXAMPLE 4

Efficacy of the subject adjuvants is further illustrated by the vaccination of cats against feline leukemia virus (FeLV). Cats were vaccinated with killed FeLV in a standard adjuvant, aluminum hydroxide and Quil-A ®, and with the virus prepared with the Pluronic ®-based adjuvant of this invention. Results indicate the Pluronic ® adjuvant-based vaccine to be substantially more protective against oronasal challenge with FeLV virus.

The feline leukemia virus used in the vaccine was a Rickard (R)-isolate originally isolated from the tissues of a leukemic cat and adapted to grow in cell culture. The persistently-infected cell line used to propagate the virus was the FC-9 cell line obtainable from Dr. Niels Pedersen, University of California at Davis, Davis, CA. The virus had been passed four times in FC-9 cells when received from Dr. Pedersen.

The growth and maintenance media used for seed and production cultures was Dulbecco's minimal essential medium (4,500 mg glucose/liter) with bovine calf serum, 2–10 percent, 10 mM HEPES buffer and antibiotics added (penicillin, up to 30 units/ml; streptomycin, up to 30 μg/ml; and mycostatin, up to 10 units/ml). The cells were grown in roller bottles of 500 cm$^2$ or 2,000 cm$^2$ surface area. Plastic or glass bottles were used for cell propagation. A cell suspension was added to the roller bottles at a ratio of $5 \times 10^7$ cells in 300–500 ml growth medium per 850 cm$^2$ roller bottle and $1.2 \times 10^8$ cells in approximately 700–1200 ml growth medium per 2,000 cm$^2$ roller bottle.

Three days following the final cell planting, a complete media change of 500 ml growth media per 850 cm$^2$ roller bottle and 1200 ml growth medium per 2,000 cm$^2$ roller bottle was done. Seven days after the final cell planting, the virus was harvested, using standard harvest techniques. Specifically, the virus fluids were aseptically transferred to harvest containers from which samples for viral titration and purity evaluation were taken. Virus produced by this method resulted in bulk virus titer greater than $10^4$ TCIF$_{50}$/ml (tissue culture infective dose per 50 ml). The virus was inactivated by addition of formalin to a final concentration of 0.3 percent. The formalin-treated fluids were maintained at approximately 20° C. for 24–72 hours under agitation and samples checked for inactivation. Merthiolate was then added to a concentration of 1:10,000.

Inactivated virus fluids were concentrated prior to the preparation of the vaccine. Virus fluids were clarified by low speed centrifugation. Fluids were concentrated by tangential flow ultrafiltration ($10^6$ MW cutoff) followed by ultracentrifugation at 19,000 rpm (Beckman T19 rotor) for 2 hours at 4° C. The resulting pellet was resuspended in phosphate buffered saline containing Merthiolate to give a concentrate equivalent to 40–300 ml of cell culture fluids per 1 ml of concentrate (milliliter equivalents).

The Pluronic ®-based vaccine was prepared as follows: The adjuvant consisted of the glycodipeptide [Thr$^1$]-MDP, squalane, Pluronic ®L-121, Tween-80 in phosphate buffered saline. The makeup of the adjuvant is as follows:

| Solution I | | |
| --- | --- | --- |
| Sodium Chloride | | 80.0 g |
| Potassium Chloride (KCl) | | 2.0 g |
| Potassium Phosphate (KH$_2$PO$_4$) | | 2.0 g |
| Dibasic Sodium Phosphate (Na$_2$HPO$_4$·7H$_2$O) | | 21.6 g |
| Tween 80 | | 40.0 ml |
| Distilled water q.s. | | 10,000.0 ml |
| Solution II | | |
| [Thr$^1$]-MDP | | 0.6 g |
| Solution I | | 50.0 ml |
| Complete adjuvant assembly: | | |
| Solution I | 84.5% | 8,450.0 ml |
| Solution II | 0.5% | 50.0 ml |
| Squalane | 10.0% | 1,000.0 ml |
| Pluronic ® L-121 | 5.0% | 500.0 ml |
| Total | 100.0% | 10,000.0 ml |

The Pluronic ®-based vaccine was formulated by mixing one part virus concentrate with one part adjuvant.

The vaccine based on aluminum hydroxide gel and Quil-A was prepared as follows: One part aluminum hydroxide gel (Alhydrogel ®), nine parts viral fluid concentrate and 50 μg of a purified saponin denoted Quil-A obtained from Superfos A/S, DK-2950 VEDBAEK, Denmark.

Two doses of the Pluronic ®-based vaccine and the aluminum hydroxide-based vaccine were administered to test cats 5 weeks and 2 weeks prior to a challenge with FeLV. The control group did not receive any injection. The cats used were specific pathogen-free domestic, short-haired kittens, 11–12 weeks old, obtained from Liberty Laboratories, P.O. Box 1, Liberty Corners, N.J., 07938.

The virus grown on FC-9 cells was used to infect the cats by the oronasal route. All cats recieved methyl prednisolone acetate (10 mg/kg) following challenge.

Weekly blood samples were obtained from all cats beginning 2 weeks post-challenge and continuing 8 weeks post-challenge. Samples were tested for viral antigens in the blood by indirect fluorescent antibody techniques and for p27 antigens by ELISA.

The results show that the use of the Pluronic ® adjuvant significantly increased the protection afforded cats when compared to the aluminum hydroxide gel/Quil-A ® adjuvant.

What is claimed is:

1. A vaccine composition comprising:
   (a) an immunologically effective amount of an antigen;
   (b) an immunopotentiating amount of an immunostimulating glycopeptide, wherein said glycopeptide is a compound of the formula

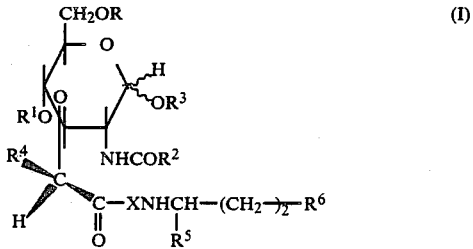

wherein
   $R$ and $R^1$ are the same or different and are hydrogen or acyl containing from 1 to 22 carbon atoms;
   $R^2$ is an unsubstituted or substituted alkyl radical containing from 1 to 22 carbon atoms, or an unsubstituted or substituted aryl radical containing from 6 to 10 carbon atoms;
   $R^3$ is hydrogen, alkyl, or aryl of 7 to 10 carbon atoms;
   $R^4$ is hydrogen or alkyl;
   X is an aminoacyl moiety selected from the group consisting of alanyl, valyl, leucyl, isoleucyl, α-aminobutyryl, threonyl, methionyl, cysteinyl, glutamyl, glutaminyl, aspartyl, phenylalanyl, tyrosyl, tryptophanyl, lysyl, ornithinyl, arginyl, histidyl, asparginyl, prolyl, hydroxyprolyl, seryl, or glycyl;
   $R^5$ and $R^6$ are the same or different and are a carboxyl group, a carboxyl group esterified with a lower alkanol, or a carbamoyl group, which, on the nitrogen atom, is unsubstituted or mono-substituted or di-substituted by alkyl, aryl, aralkyl, alkylidene, or carbamoylmethyl;
   (c) a multi-phase-forming amount of a non-toxic polyoxypropylene-polyoxyethylene block polymer, wherein said block polymer is liquid over a temperature range between about 15°–40° C., has a polyoxypropylene midsection of molecular weight between about 2250 and 4300, and has polyoxyethylene in an amount between about 1 and 30% of the block polymer;
   (d) a multi-phase-stabilizing amount of a glycol ether-based surfactant; and
   (e) buffered isoosmotic saline in a quantity sufficient to make volume.

2. The vaccine of claim 1 having the glycopeptide of Formula (I) wherein
   $R$ and $R^1$ are the same or different and are hydrogen or an acyl radical containing from 1 to 22 carbon atoms;
   $R^2$ is methyl;
   $R^3$ is hydrogen; and
   X is L-seryl, L-alanyl, L-valyl, L-leucyl, L-isoleucyl, L-α-aminobutyryl, L-threonyl, L-methionyl, L-cysteinyl, L-phenylalanyl, L-tyrosyl, L-tryptophenyl, L-lysyl, L-ornithyl, L-arginyl, L-histidyl, L-glutamyl, L-glutamanyl, L-aspartyl, L-asparaginyl, L-prolyl, or L-hydroxyprolyl.

3. The vaccine of claim 2 wherein said glycopeptide is a compound of Formula (I) wherein
   $R$, $R^1$ and $R^3$ are hydrogen;
   $R^2$ is methyl;
   $R^4$ is methyl, butyl or hydrogen;
   X is L-valyl, L-alanyl, L-seryl, L-threonyl or L-α-aminobutyryl;
   $R^5$ is carboxyl, carbamoyl or n-butyl carboxylate; and
   $R^6$ is carboxyl or carbamoyl.

4. The vaccine of claim 3 wherein said glycopeptide is
   N-acetylmuramyl-L-α-aminobutyryl-D-isoglutamine;
   6-O-stearoyl-N-acetylmuramyl-L-α-aminobutyryl-D-isoglutamine;
   N-acetylmuramyl-L-threonyl-D-isoglutamine;
   N-acetylmuramyl-L-valyl-D-isoglutamine;
   N-acetylmuramyl-L-alanyl-D-isoglutamine;
   N-acetyl-desmethylmuramyl-L-alanyl-D-isoglutamine;
   N-acetylmuramyl-L-alanyl-D-glutamine n-butyl ester;
   N-acetylmuramyl-L-seryl-D-isoglutamine;
   N-acetyl(butylmuramyl)-L-α-aminobutyl-D-isoglutamine; or
   N-acetyl(butylmuramyl)-L-alanyl-D-isoglutamine.

5. The vaccine of claim 4 wherein said glycopeptide is
   N-acetylmuramyl-L-threonyl-D-isoglutamine;
   N-acetylmuramyl-L-α-aminobutyryl-D-isoglutamine;
   N-acetyl-desmethylmuramyl-L-alanyl-D-isoglutamine; or
   N-acetyl(butylmuramyl)-L-α-aminobutyl-D-isoglutamine.

6. The vaccine of claim 5 wherein said glycopeptide is N-acetylmuramyl-L-threonyl-D-isoglutamine.

7. The vaccine of claim 5 wherein the glycopeptide is present in a concentration range of 0.001–5% (w/w).

8. The vaccine of claim 7 wherein the glycopeptide is present in a concentration range of 0.001–3%.

9. The vaccine of claim 1 wherein the antigen is a cholera, diptheria, tetanus, pertussis, meningitis, plague, or typhoid antigen.

10. The vaccine of claim 1 wherein the antigen is a influenza, measles, meningitis, mumps, poliomyelitis, rabies, rubella, smallpox, or yellow fever antigen.

11. The vaccine of claim 1 wherein the antigen is a Rocky Mountain spotted fever or typhus rickettsiae antigen.

12. The vaccine of claim 1 wherein said block polymer has a polyoxypropylene midsection of molecular weight between 3,250 and 4,000 and the percent polyoxyethylene in the block polymer comprises 0.2 to 49% (w/w).

13. The vaccine of claim 12 wherein said block polymer has a polyoxypropylene midsection of molecular weight between 3,250 and 4,000 and the percent polyoxyethylene in the block polymer comprises 0.2 to 20% (w/w).

14. The vaccine of claim 1 wherein said block polymer has a polyoxypropylene midsection of molecular weight between 2,250 and 4,300 and wherein the percentage of polyoxyethylene in the block polymer is 1–30% (w/w).

15. The vaccine of claim 14 wherein said block polymer is comprised of a polyoxypropylene midsection of molecular weight 3550 has a percentage polyoxyethylene in the block polymer of 10%.

16. The vaccine of claim 1 wherein the block polymer is present in an amount of 0.2–49% (v/v).

17. The vaccine of claim 16 wherein the block polymer is present in an amount of 0.2–20% (v/v).

18. The vaccine of claim 17 wherein the block polymer is present in an amount of 1–5% (v/v).

19. The vaccine of claim 18 wherein the block polymer is present in an amount of 2.5% (v/v).

20. The vaccine of claim 1 wherein said surfactant is a sorbitan-based surfactant.

21. The vaccine of claim 20 wherein said surfactant is polyoxyethylene 20 sorbitan monooleate.

22. The vaccine of claim 1 wherein said surfactant is present in an amount of 0.05–2.5% (w/w).

23. The vaccine of claim 22 wherein said surfactant is present in an amount of 0.2–1% (w/w).

24. The vaccine of claim 1 which further comprises a non-toxic metabolizable oil, present in an amount of 1–30% (w/w).

25. A vaccine for immunizing an animal against chlorea, diptheria, tetanus, pertussis, influenza, measles, meningitis, mumps, plague, poliomyelitis, rabies, Rocky Mountain spotted fever, rubella, smallpox, typhoid, typhus, or yellow fever, which vaccine comprises:
(a) an immunologically effective amount of a cholera, diptheria, tetanus, pertussis, influenza, measles, meningitis, mumps, plague, poliomyelitis, rabies, Rocky Mountain spotted fever, rubella, smallpox, typhoid, typhus, or yellow fever antigen;
(b) 0.001–5% (w/w) immunostimulating glycopeptide, wherein said glycopeptide is a compound of the formula

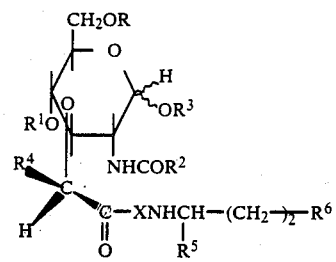

wherein
R and $R^1$ are the same or different and are hydrogen or acyl containing from 1 to 22 carbon atoms;
$R^2$ is an unsubstituted or substituted alkyl radical containing from 1 to 22 carbon atoms, or an unsubstituted or substituted aryl radical containing from 6 to 10 carbon atoms;
$R^3$ is hydrogen, alkyl, or aryl of 7 to 10 carbon atoms;
$R^4$ is hydrogen or alkyl;
X is an aminoacyl moiety selected from the group consisting of alanyl, valyl, leucyl, isoleucyl, α-aminobutyryl, threonyl, methionyl, cysteinyl, glutamyl, glutaminyl, aspartyl, phenylalanyl, tyrosyl, tryptophanyl, lysyl, ornithinyl, arginyl, histidyl, asparginyl, prolyl, hydroxyprolyl, seryl, or glycyl;
$R^5$ and $R^6$ are the same or different and are a carboxyl group, a carboxyl group esterified with a lower alkanol, or a carbamoyl group, which, on the nitrogen atom, is unsubstituted or mono-substituted or di-substituted by alkyl, aryl, aralkyl, alkylidene, or carbamoylmethyl;
(c) 0.2–20% (w/w) multi-phase-forming, non-toxic polyoxypropylene-polyoxyethylene block polymer, wherein said block polymer is liquid over a temperature range between about 15°–40° C., has a polyoxypropylene midsection of molecular weight between about 2250 and 4300, and has polyoxyethylene in an amount between about 1 and 30% of the block polymer;
(d) 0.05–2.5% (w/w) multi-phase-stabilizing glycol ether-based surfactant; and
(e) phosphate-buffered saline.

26. The vaccine of claim 25 wherein:
(a) said antigen is inactivated virus;
(b) said block polymer is present in an amount of 2.5% (w/w); and
(c) said surfactant is present in an amount of 0.2–1% (w/w).

27. The vaccine of claim 26 wherein:
(a) said glycopeptide is N-acetylmuramyl-L-threonyl-D-isoglutamine present in an amount of 0.03% (w/w); and
(b) said block polymer has a polyoxypropylene midsection of molecular weight between 3,250 and 4,000 and the percent polyoxyethylene in the block polymer comprises 0.2 to 20% (w/w).

28. The vaccine of claim 27 which further comprises a non-toxic metabolizable oil, present in an amount of 1–30% (w/w).

* * * * *

UNITED STATES PATENT AND TRADEMARK OFFICE
CERTIFICATE OF CORRECTION

PATENT NO. : 4,772,466

DATED : September 20, 1988

INVENTOR(S) : Anthony C. Allison and Noelene Byars

It is certified that error appears in the above-identified patent and that said Letters Patent is hereby corrected as shown below:

On the Cover Page, within the "Notice" section, "Aug. 12, 2003" should read -- Aug. 19, 2003 --.

In Column 3, line 61, "PLURONTC®" should read -- PLURONIC® --.

In Column 5, line 23, "SPAN" should read -- SPAN® --; and "ARLACEL" should read -- ARLACEL® --.

In Column 8, line 28, "$R_3$" should read -- $R^3$ --.

In Claim 3, line 3, "$R_3$" should read -- $R^3$ --.

In Claim 8, line 2, "0.001-3%" should read -- 0.01 to 3% --.

In Claim 27, line 3, "0.03%" should read -- 0.003% --.

Signed and Sealed this

Seventh Day of February, 1989

Attest:

DONALD J. QUIGG

Attesting Officer     Commissioner of Patents and Trademarks